(12) United States Patent
Jing et al.

(10) Patent No.: US 8,203,007 B2
(45) Date of Patent: Jun. 19, 2012

(54) BIFUNCTIONAL LACTIDE MONOMER DERIVATIVE AND POLYMERS AND MATERIALS PREPARED USING THE SAME

(75) Inventors: Feng Jing, Saint Paul, MN (US); Marc Hillmyer, Minneapolis, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 499 days.

(21) Appl. No.: 12/479,981

(22) Filed: Jun. 8, 2009

(65) Prior Publication Data

US 2009/0306333 A1 Dec. 10, 2009

Related U.S. Application Data

(60) Provisional application No. 61/131,207, filed on Jun. 6, 2008.

(51) Int. Cl.
*C07D 313/20* (2006.01)

(52) U.S. Cl. ............. 549/265; 549/13; 549/49; 549/269

(58) Field of Classification Search .................... 549/13, 549/49, 265, 269

See application file for complete search history.

(56) References Cited

OTHER PUBLICATIONS

USPTO search report, Jan. 2012.*
Love et al., "A Practical and Highly Active Ruthenium-Based Catalyst that Effects the Cross Metathesis of Acrylonitrile," Angew. Chem. Int. Ed. 41(21): 4035-37, 2002.

* cited by examiner

*Primary Examiner* — Gregory Listvoyb

(74) *Attorney, Agent, or Firm* — Shumaker & Sieffert, P.A.

(57) ABSTRACT

The invention described herein provides a novel lactide monomer derivative and process for preparing the lactide monomer derivative. The monomer derivative of the invention is bifunctional in nature, and can be employed a variety of efficient synthesis processes to prepare various polymers. Further, the bifunctional monomer derivative can be used to prepare various intermediate-stage compounds and polymers, which in turn can be used to synthesize other compounds, polymers, copolymers and composites. The lactide monomer derivative has a bifunctional norbornene spiro lactide structure, spiro[6-methyl-1,4-dioxane-2,5-dione-3,2'-bicyclo[2.2.1]hept[5]ene], and structure as follows:

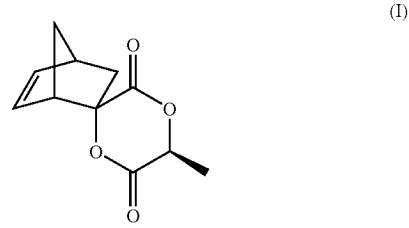

(I)

and stereoisomers thereof. The lactide monomer derivative is bifunctional in that either 1) the norbornene ring, 2) lactide ring, or 3) both, can be opened and used in polymer synthesis for the backbone or the reactive branch for other polymeric syntheses.

3 Claims, 10 Drawing Sheets

500 MHz $^1$H NMR and 125 MHz $^{13}$C NMR spectra of spiro[6-methyl-1,4-dioxane-2,5-dione-3,2'-bicyclo[2.2.1]hept[5]ene] in CDCl$_3$ 500 MHz ¹HNMR spectrum of poly(8-methyl-6,9-dioxa-spiro[4.5]decane-7,10-dione-1,3-diylvinylene) in $CDCl_3$ SEM images of composite poly(8-methyl-6,9-dioxa-spiro[4.5]decane-7,10-dione-1,3-diylvinylene)-co-poly(but-1-ene-1,4-diyl)-branch-poly(DL-lactide)-blend-poly(DL-lactide) (A:secondary electron image, B: backscattered electron image). The surface was cryo-microtomed, stained by 0.5% $RuO_4$ solution vapor for 30 min, and then coated with ~2 nm of Pt by direct Pt sputtering.

SEM images of binary blends of polycyclooctadiene and poly(DL-lactide) (A: secondary electronimage, B: backscattered electron image). The surface was cryo-microtomed, stained by 0.5% $RuO_4$ solution vapor for 30 min, and then coated with ~2 nm of Pt by direct Pt sputtering TEM images of composite poly(8-methyl-6,9-dioxa-spiro[4.5]decane-7,10-dione-1,3-diylvinylene)-co-poly(but-1-ene-1,4-diyl)-branch-poly(DL-lactide)-blend-poly(DL-lactide). The thin film was stained by 4% $OsO_4$ solution vapor for 15 min before imaging.

Tensile tests on composite poly(8-methyl-6,9-dioxa-spiro[4,5]decane-7,10-dione-1,3-diylvinylene)-co-poly(but-1-ene-1,4-diyl)-branch-poly(DL-lactide)-blend-poly(DL-lactide) (C) and binary blends of polycyclooctadiend and poly(DL-lactide) (B).

BIFUNCTIONAL LACTIDE MONOMER DERIVATIVE AND POLYMERS AND MATERIALS PREPARED USING THE SAME

RELATED APPLICATION DATA

This application claims benefit of priority to Provisional Application Ser. No. 61/131,207, filed Jun. 6, 2008.

STATEMENT OF GOVERNMENT INTEREST

This invention has been funded in part by the United States Department of Agriculture via Grant No. 68-3A75-6-504. The U.S. Government has certain rights in this invention.

BACKGROUND OF THE INVENTION

Polylactic acid or polylactide (a.k.a. PLA) is a biorenewable, biocompatible and biodegradable thermoplastic polyester derived from the cyclic ester lactide. Polylactide is well-known to be useful in a variety of applications in a wide variety of fields and technologies. Examples of useful poly-D-lactide (PDLA) and poly-L-lactide (PLLA) products include, but are not limited to, upholstery, microwavable trays, clothing materials and fabrics, engineering plastics, medical devices (e.g., sutures, stents) and drug delivery formulations. Polylactide biodegradability properties make it useful for disposable packaging materials and disposable items, such as garments and feminine hygiene products.

Polylactide can be derived from renewable resources, such as corn starch or sugarcane. Typically, bacterial fermentation can be used to produce lactic acid from corn starch or cane sugar. Because of the difficulties associated with achieving high molecular weight, the direct polymerization of lactic acid is not ideal for producing useful products. Lactic acid is, therefore, used to prepare oligomers which are then dimerized using a catalyst to prepare a cyclic lactide monomer. Ring-opening of lactide leads to higher molecular weight polylactide using stannous octoate catalyst or tin (II) chloride, for example.

There has been interest in the polymer field of preparing polylactide derivatives that exhibit enhanced properties as compared to unmodified polylactide, such as higher glass transition temperature, improved thermal stability, controlled crystallinity, reduced water absorption, increased toughness, and the like. Efforts to derivatize polylactide have often been associated with the objective of producing a polylactide that mimics the benefits associated with petroleum-based polymers while still possessing "biofriendliness." Alkly-, alkenyl-, and aryl-substituted glycolides and glycolides with protected pendant carboxyl, hydroxyl, and amino groups have been prepared from corresponding alpha-hydroxyacids of variable origin and polymerized. Generally, polylactide-containing materials continue to be of significant interest in the field of consumer materials such as containers and packaging, due to their biorenewability, biocompatibility and biodegradability properties. Difficulty has been encountered, however, in balancing the biodegradability of materials with durability and toughness.

Poly-L-lactide (PLLA) can have a glass transition temperature ($T_g$) from about 50° C. to about 70° C. and a melting temperature between about 173° C. and about 178° C. One disadvantage with existing polylactide derivatives is that the resultant polylactide exhibits relatively low glass transition temperatures and is, therefore, not suitable as a containment or packaging material that experience elevated temperature environmental conditions and/or contents. Another disadvantage associated with polylactide-based materials is their long-term durability, brittleness, and cracking over time.

There exists a need in the polymer field for improved lactide monomer derivatives and polymerization processes that could utilize such monomers in the preparation of polylactide-derived materials. There further exists a need in the field of polymer products for thermoformable materials that are capable of withstanding elevated temperature conditions while still exhibiting biorenewability, biocompatibility and biodegradability. Still further, there is a need to develop materials that balance the biodegradability of the polylactide material with the toughness, durability and water transport control properties desired for its use for containment and packaging.

SUMMARY OF THE INVENTION

The invention provides a novel lactide monomer derivative and process for preparing the lactide monomer derivative. It has been discovered that a unique monomer could be developed which is bifunctional in nature, and which in turn can be employed a variety of efficient synthesis processes to prepare various polymers. Furthermore, various polymers that can be prepared using the lactide monomer derivative as part of the process exhibit enhanced and improved properties and chemical behaviors as compared to conventionally used monomers and known polymers in similar and different applications. The invention and its various aspects of usage can be used in a wide variety of industrial contexts, including thermoformed medical plastic products and consumer packaging. Particularly advantageous and beneficial is that, because the monomer, polymers and polymeric composites prepared therewith, are lactide-based, the products are associated with biodegradability, biorenewability and biocompatibility attributes. Thus the invention can be associated with environmentally-friendly manufacturing processes and products, while at the same time can exhibit durability and toughness properties desirable for consumer and containment materials. Yet another advantage associated with the invention is that the bifunctional monomer derivative can be used to prepare various intermediate-stage compounds and polymers, which in turn can be used to synthesize other compounds, polymers, copolymers and composites.

The invention provides a lactide monomer derivative having a bifunctional norbornene spiro lactide structure, spiro[6-methyl-1,4-dioxane-2,5-dione-3,2'-bicyclo[2.2.1]hept[5]ene], and as follows:

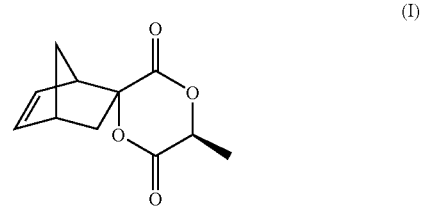

(I)

and stereoisomers thereof. The lactide monomer derivative is bifunctional in that either 1) the norbornene ring, 2) lactide ring, or 3) both, can be opened and used in polymer synthesis for the backbone or the reactive branch for other polymeric syntheses.

The invention also provides a process for preparing spiro [6-methyl-1,4-dioxane-2,5-dione-3,2'-bicyclo[2.2.1]hept[5] ene] (Formula (I)) comprising: a) reacting L-lactide with N-bromosuccimide to prepare a brominated intermediate compound 3-bromo-3,6-1,4-dioxane-2,5-dione; b) reacting 3-bromo-3,6-1,4-dioxane-2,5-dione with a tertiary amine, preferably triethylamine, to prepare 3-methyl-6-methylene-1,4-dioxane-2,5-dione; and c) reacting 3-methyl-6-methylene-1,4-dioxane-2,5-dione with cyclopentadiene, to prepare spiro[6-methyl-1,4-dioxane-2,5-dione-3,2'-bicyclo[2.2.1]hept[5]ene].

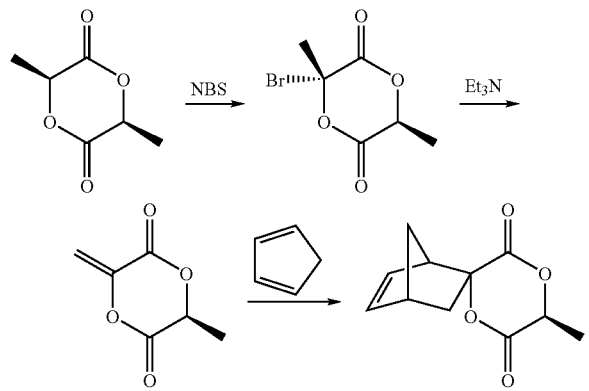

The invention also provides a lactide ring-opened homopolymer composed of repeating units of norbornene ring-substituted polylactide and having the following structural formula:

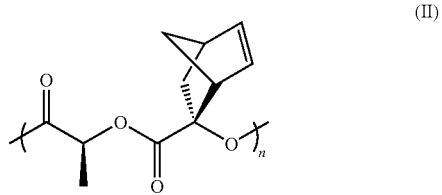

(II)

wherein n is an integer, prepared from a ring opening polymerization (ROP) process using the lactide monomer derivative of structural formula (I).

The invention further provides a process for preparing the lactide-opened homopolymer comprising: reacting spiro[6-methyl-1,4-dioxane-2,5-dione-3,2'-bicyclo[2.2.1]hept[5]ene] with a catalyst and initiator using ring-opening polymerization (ROP). The catalyst can comprise a strong base such as 1,5,7-triazabicyclo[4.4.0]dec-5-ene, and the initiator can comprise a primary alcohol such as benzyl alcohol.

The invention also provides a norbornene ring-opened homopolymer composed of repeating units of lactide-substituted polynorbornene and having the following structural formula:

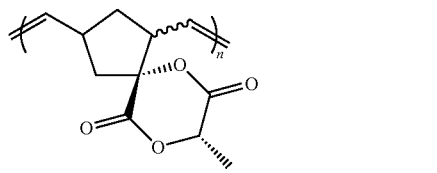

wherein n is an integer.

The invention provides a process for preparing norbornene ring-opened homopolymer composed of repeating units of lactide-substituted polynorbornene comprising: reacting spiro[6-methyl-1,4-dioxane-2,5-dione-3,2'-bicyclo[2.2.1]hept[5]ene] with a third generation Grubbs' catalyst via ring opening metathesis polymerization (ROMP).

In yet another aspect, the invention provides a lactide-functionalized polycycloolefin/polynorbornene-backboned copolymer prepared using the spiro lactide monomer derivative of the invention. In one embodiment, the invention provides a lactide ring functionalized polycycloocctadiene/polynorbornene-backboned copolymer poly(8-methyl-6,9-dioxa-spiro[4.5]decane-7,10-dione-1,3-diylvinylene)-co-poly(but-1-ene-1,4-diyl) having the following chemical structure:

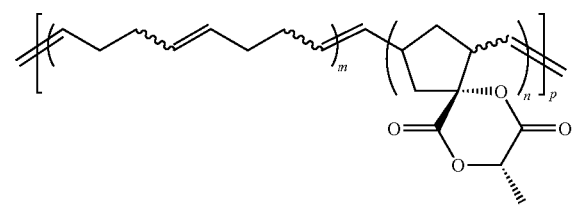

wherein m, n and p are each integers, prepared from the reaction using lactide monomer derivative of formula (I) with cyclooctadiene. The prepared lactide ring functionalized polycyclooctadiene itself can be useful as an intermediate for the preparation of other materials by utilizing the lactide ring groups on the polymer for subsequent grafting and/or cross-linking reactions, for example.

The invention also provides a process for preparing lactide-branched polycycloolefin or polycycloalkene copolymers using the monomer derivative of the invention. In one embodiment, a polycyclooctadiene-co-polynorbornene with lactide ring groups copolymer (poly(8-methyl-6,9-dioxa-spiro[4.5]decane-7,10-dione-1,3-diylvinylene)-co-poly(but-1-ene-1,4-diyl)) comprising reacting cyclooctadiene and spiro[6-methyl-1,4-dioxane-2,5-dione-3,2'-bicyclo[2.2.1]hept[5]ene] in the presence of a second generation Grubbs' catalyst and chain transfer agent.

The invention further provides a polymeric composite material prepared from reacting the lactide branched polyolefin e.g., polycyclooctadiene-backboned copolymer poly(8-methyl-6,9-dioxa-spiro[4.5]decane-7,10-dione-1,3-diylvinylene)-co-poly(but-1-ene-1,4-diyl)) with free DL-lactide and having the following chemical structure:

poly(DL-lactide) +

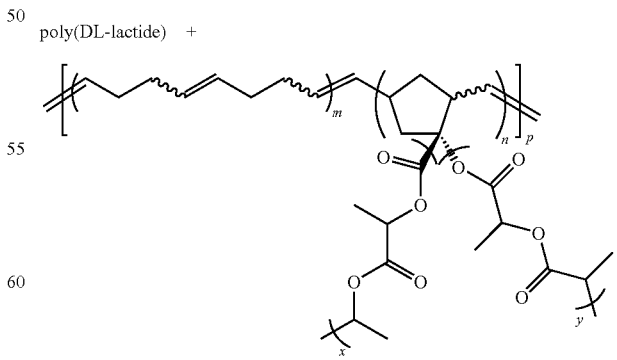

wherein m, n, p, x and y are each integers.
The composite above exhibits enhanced toughness and possibly better water transport properties as compared to conventional polylactide materials. One advantage associated with the invention is that relatively minor amounts of the lactide branched polycyclooctadiene polymers prepared using the lactide monomer derivative and process of the invention are needed to have substantial effect on the desired properties of the resulting composite. In one embodiment, only about 20% of the lactide branched polycyclooctadiene polymers can be present in the composite with about 80% poly(DL-lactide) to prepare a composite exhibiting enhanced toughness. Aside form its mechanical properties, the polymer composite material can still maintain partial biodegradability and afford cost-effective manufacturing.

The invention also provides a process for preparing a lactide branched polycyclooctadiene by reacting a lactide ring-functionalized polycyclooctadiene with free DL-lactide using a ring opening polymerization process in the presence of a catalyst and initiator. In one embodiment, the catalyst can be a strong base such as 1,5,7-triazabicyclo[4.4.0]dec-5-ene and the initiator can be a primary alcohol such as benzyl alcohol.

Lactide branched polymers with lactide ring either intact or opened can in turn be used to prepare various other polymers, e.g., by crosslinking, and the like. Additionally, variations on the processes using the spiro[6-methyl-1,4-dioxane-2,5-dione-3,2'-bicyclo[2.2.1]hept[5]ene] monomer derivative of the invention are possible as well.

These and other advantages will become apparent from the following disclosure.

BRIEF DESCRIPTION OF THE DRAWINGS

The invention is further illustrated by the following drawings—none of which is intended to be construed as necessarily limiting the invention.

DETAILED DESCRIPTION OF THE INVENTION

As used herein, the term "comprising" means the elements recited, or their equivalent in structure or function, plus any other element(s) which are not recited. The terms "having" and "including" are also to be construed as open ended unless the context suggests otherwise. Terms such as "about", "generally", "substantially" and the like are to be construed as modifying a term or value such that it is not an absolute, but does not read on the prior art. Such terms will be defined by the circumstances and the terms that they modify are understood by those of skill in the art. This includes at the very least the degree of expected experimental error, technique error, and instrument error for a given technique used to measure a value.

The term "high glass transition temperature" as used in the context of describing properties of polymers prepared in accordance with the invention is meant as a relative term in comparison to lower glass transition temperature polylactides and lactide-based compounds which are known in the art.

The term "bifunctional" when used to describe the lactide monomer derivative of the invention is meant to refer to the dual nature of the cleavable ring opening possibilities, i.e., the norbornene ring and lactide ring, associated with the structural formula.

The term "polylactide-based" as used herein is meant to refer to the significant presence of polymers prepared and/or derived from the lactide ring structure.

Bifunctional Monomer Derivative

The invention includes a bifunctional monomer derivative having a norbornene spiro lactide structure. Specifically, the monomeric compound is spiro[6-methyl-1,4-dioxane-2,5-dione-3,2'-bicyclo[2.2.1]hept[5]ene], and has a structural formula as follows:

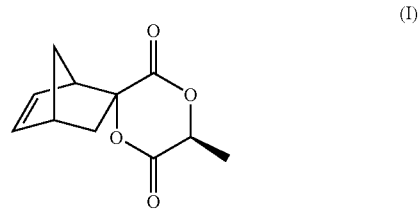

(I)

and stereoisomers thereof.

Example 1

Preparation of the Bifunctional Norbornene Spiro Lactide Monomer Derivative

Figure 1:
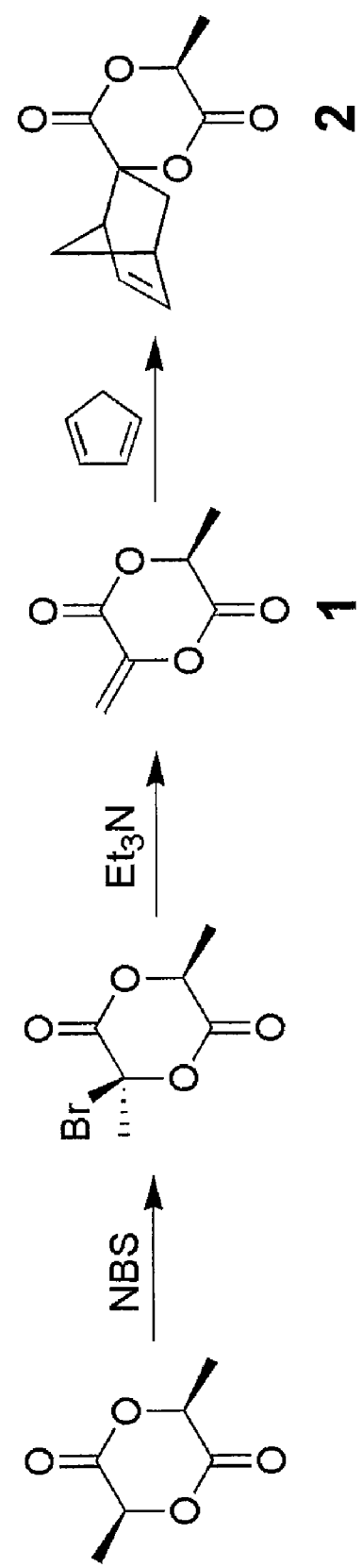
FIG. 1 is a chemical reaction diagram showing the preparation of the lactide monomer derivative spiro[6-methyl-1,4-dioxane-2,5-dione-3,2'-bicyclo[2.2.1]hept[5]ene] using the bromination-elimination technique, according to one embodiment of the invention.

The spiro[6-methyl-1,4-dioxane-2,5-dione-3,2'-bicyclo[2.2.1]hept[5]ene] monomer derivative of the invention can be prepared using the lactide compound (e.g., S,S-lactide (L-lactide), D-lactide or DL-lactide) as the starting material to prepare the intermediate compound 3-methyl-6-methylene-1,4-dioxane-2,5-dione. For this process, a bromine addition and elimination reaction on the lactide compound can be employed as illustrated in FIG. 1.

3-Bromo-3,6-dimethyl-1,4-dioxane-2,5-dione was prepared by adding L-lactide (200.0 g, 1.388 mol), benzene (1 L) and N-bromosuccimide (272.0 g, 1.528 mol) to a 2 L three-neck flask. The mixture was brought to a reflux under mechanical stirring. Benzoyl peroxide (6.72 g, 27.7 mmol) in benzene (100 mL) was then added dropwise through a dropping funnel over 20 minutes. After the monomer was consumed, the reaction mixture was cooled to room temperature, and the solid filtered off. The filtrate was evaporated to dryness forming a pale yellow solid. The solid was dissolved in dichloromethane (1.5 L) and the solution was washed with saturated sodium bisulfite solution three times and saturated NaCl once. The organic layer was dried over $MgSO_4$, and the solution was evaporated to dryness. The orange solid was recrystallized from ethyl acetate and hexanes to give 137.9 g of white crystal. The mother liquor from the filtration was evaporated to dryness, and the solid was recrystallized from ethyl acetate and hexanes to give 54.3 g white crystal. In total, the yield was 192.2 g (62%).

The brominated intermediate (31.2 g, 0.140 mol) was added into a 500 mL three-neck flask along with 200 mL dichloromethane. The flask was protected under nitrogen and cooled in an ice bath. Triethylamine (21.5 mL, 0.154 mol) was added dropwise.

Tertiary amines having substantially similar basicities to triethylamine can be used in this process step. Preferred for use in this process step, however, is triethylamine (shown in the figures as $Et_3N$).

After one hour in the ice bath, the reaction was brought to room temperature and stirred for an additional one hour, transferred to a separatory funnel, and washed with 1 M HCl three times and saturated NaCl once. The organic layer was dried over $MgSO_4$ and the solvent was evaporated. The pale yellow solid was then purified by silica gel column chromatography (dichloromethane, $r_f$=0.41) to yield a white solid. The solid was further purified by sublimation at 45° C. under vacuum yielding 11.88 g (60%) of white crystal.

Figure 2:
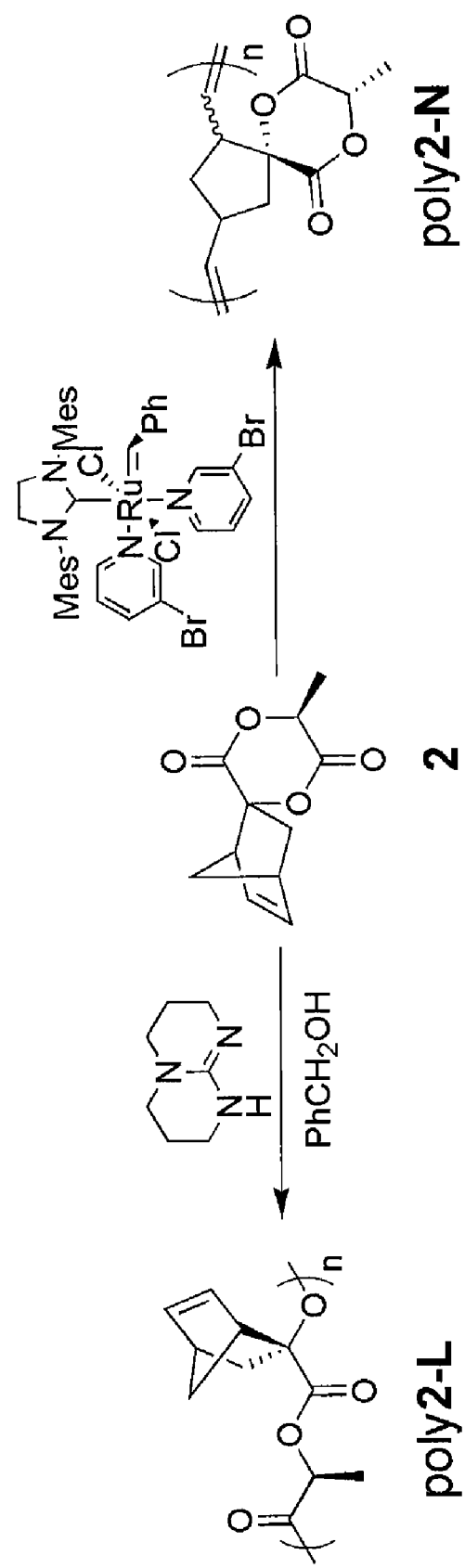
FIG. 2 is a chemical reaction diagram showing two possible ring-opening polymerization pathways using the same spiro[6-methyl-1,4-dioxane-2,5-dione-3,2'-bicyclo[2.2.1]hept[5]ene] monomer derivative, according to the invention.

To then prepare the norbornene spiro lactide monomer compound, 3-methyl-6-methylene-1,4-dioxane-2,5-dione can be used as a dioenophile (as a captodative alkene, i.e., an alkene substituted with both electron withdrawing and electron donating groups) by Diels-Alder reaction to prepare spiro[6-methyl-1,4-dioxane-2,5-dione-3,2'-bicyclo[2.2.1]hept[5]ene]. In this stage and as depicted in FIG. 2, using the 3-methyl-6-methylene-1,4-dioxane-2,5-dione as the dieneophile and reacting with cyclopentadiene.

Figure 4:
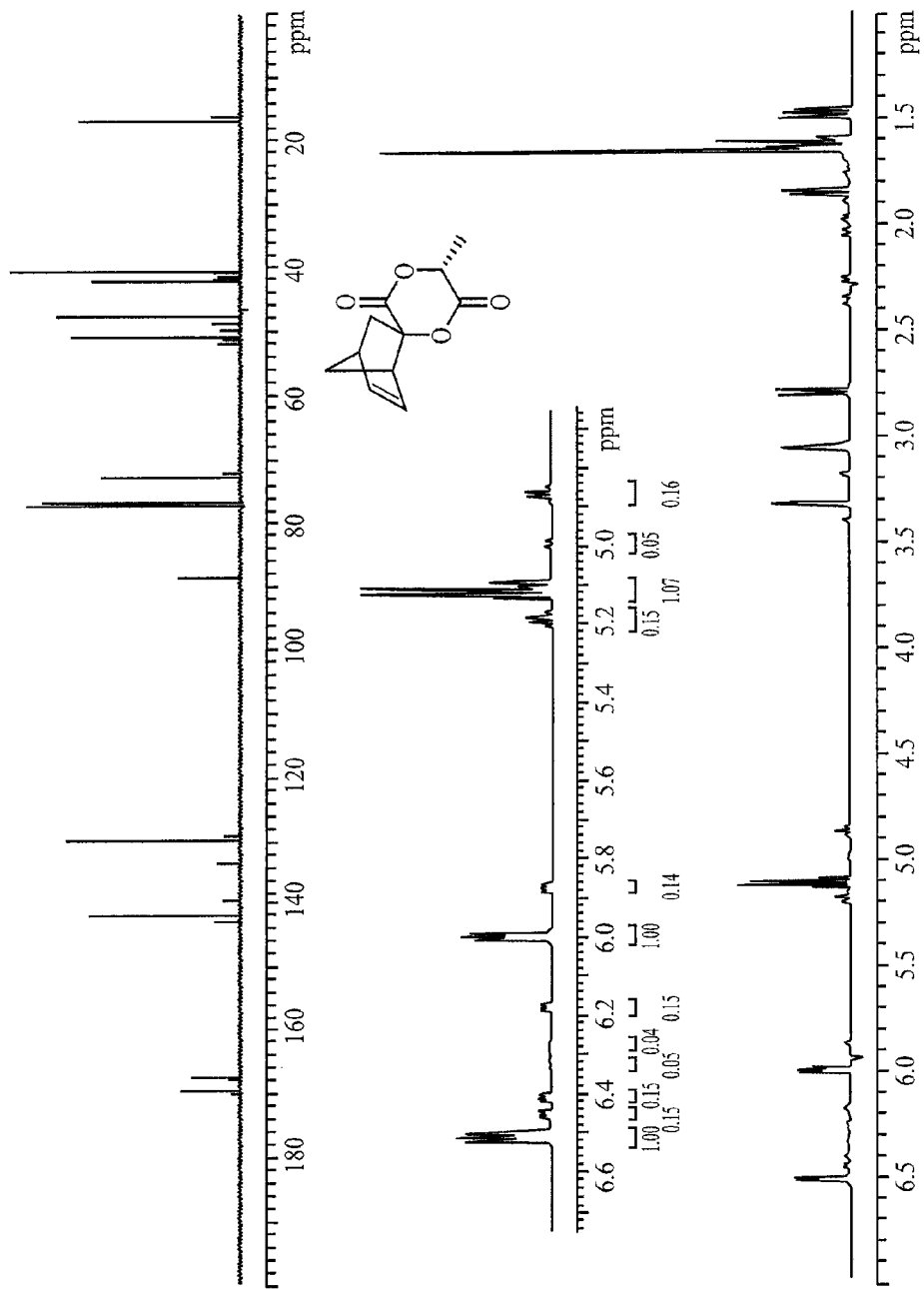
FIG. 4 is NMR spectra graphs of spiro[6-methyl-1,4-dioxane-2,5-dione-3,2'-bicyclo[2.2.1]hept[5]ene] monomer of the invention.

To a 250 mL flask, 3-methyl-6-methylene-1,4-dioxane-2,5-dione (15.0 g, 0.106 mol) was added, along with distilled cyclopentadiene (14.0 g, 0.212 mol) and benzene (100 mL). The reaction mixture was refluxed overnight under Argon. After cooling the mixture to room temperature, benzene and extra cyclopentadiene were removed by rotary evaporation. The crude product was then purified by silica gel column chromatography, first by hexanes to remove dicyclopentadiene, followed by dichloromethane ($r_f$=0.31). The solid was then further purified by sublimation at 50° C. under vacuum to give 20.74 g (94%) white crystal. $^1$H NMR spectra data of the product is shown in FIG. 4.

This reaction produces four pairs of enantiomers due to the endo and exo forms of the tricycle. From these, a preferred cycloadduct was selected, which exhibited high diastereofacial selectivity as expected from the methyl group being on opposite side from the cyclopentadiene to minimize steric repulsion. High exo selectivity was observed as well consistent with the preference for anti-Alder addition observed for other captodative dieneophiles.

An important aspect of the invention is that the bifunctionality of the monomer unit of the invention can be selectively reacted in its structural portions. Put another way, either the norbornene ring portion, lactide ring portion, or both, can be utilized in compound and polymer synthesis. For instance, the norbornene ring can be selectively cleaved without opening the lactide ring structure. Likewise, the lactide ring structure can be cleaved without opening the norbornene ring portion. At this modified monomer stage alone, the monomer derivative of the invention permits two synthesis pathways as illustrated in the second reaction shown in FIG. 2—each of which can produce chemically distinct entities associated with various chemical properties.

Lactide Ring-Opened Homopolymer

In another aspect of the invention, the spiro[6-methyl-1,4-dioxane-2,5-dione-3,2'-bicyclo[2.2.1]hept[5]ene] monomer derivative can be used to synthesize a lactide ring-opened homopolymer, which itself can be used to further synthesize other polymers.

Example 2

Preparation of Lactide Ring-Opened Polymer

A lactide-opened homopolymer poly(oxy-1-oxoethylene-2-bicyclo[2.2.1]hept-5-ene) can be prepared by ring opening polymerization (ROP) of the highly sterically hindered spiro[6-methyl-1,4-dioxane-2,5-dione-3,2'-bicyclo[2.2.1]hept[5]ene]. In a dry box, a catalyst/initiator solution was prepared by adding 1,5,7-triazabicyclo[4.4.0]dec-5-ene (TBD) (6.7 mg, 48 μmol), benzyl alcohol (10.0 μL, 96 μmol) and anhydrous $CH_2Cl_2$ (9.6 mL) to a 20 mL vial. To a 20 mL pressure vessel was added spiro[6-methyl-1,4-dioxane-2,5-dione-3,2'-bicyclo[2.2.1]hept[5]ene] (0.20 g, 0.96 mmol) and the catalyst/initiator solution (0.96 mL).

Variations of catalyst and initiator combinations are possible for this reaction step. For example, other strong bases that could possibly be used as the catalyst in place of TBD include 1,8-diazabicycloundec-7-ene (a.k.a. DBU) and N-methyl TBD. Primary alcohols can be used as the initiator in this process step as well, in place of or in addition to, benzyl alcohol. Primary alcohols are preferred in light of the spiro monomer structure.

After a period of 24 hours, the reaction was quenched by addition of excess (>10 equivalents) of benzoic acid, and the solution evacuated to dryness and analyzed by H NMR and GPC. The remaining polymer solution was precipitated into methanol three times. The formed solid polymer sample was vacuum dried overnight and analyzed by NMR, GPC and DSC.

The resulting lactide-opened homopolymer (poly(oxy-1-oxoethylene-2-bicyclo[2.2.1]hept-5-ene) has the following structural formula:

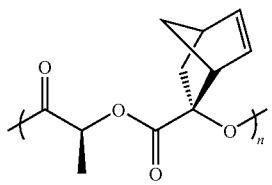

wherein n is an integer.

At about 3 hours, about 81% conversion of the monomer can be achieved (100 eq [monomer]$_0$=1.0 M in CH$_2$Cl$_2$) under ambient temperature conditions, and conversion of about 84% can be achieved over a period of 24 hours (the reaction quenched with 10 eq benzoic acid). The relative molecular mass M$_n$ (SEC, polystyrene standards) of an opened polylactide chain having norbornene side groups at 24 hours was 4.9 kg mol$^{-1}$ and PDI was 1.85.

Figure 5:
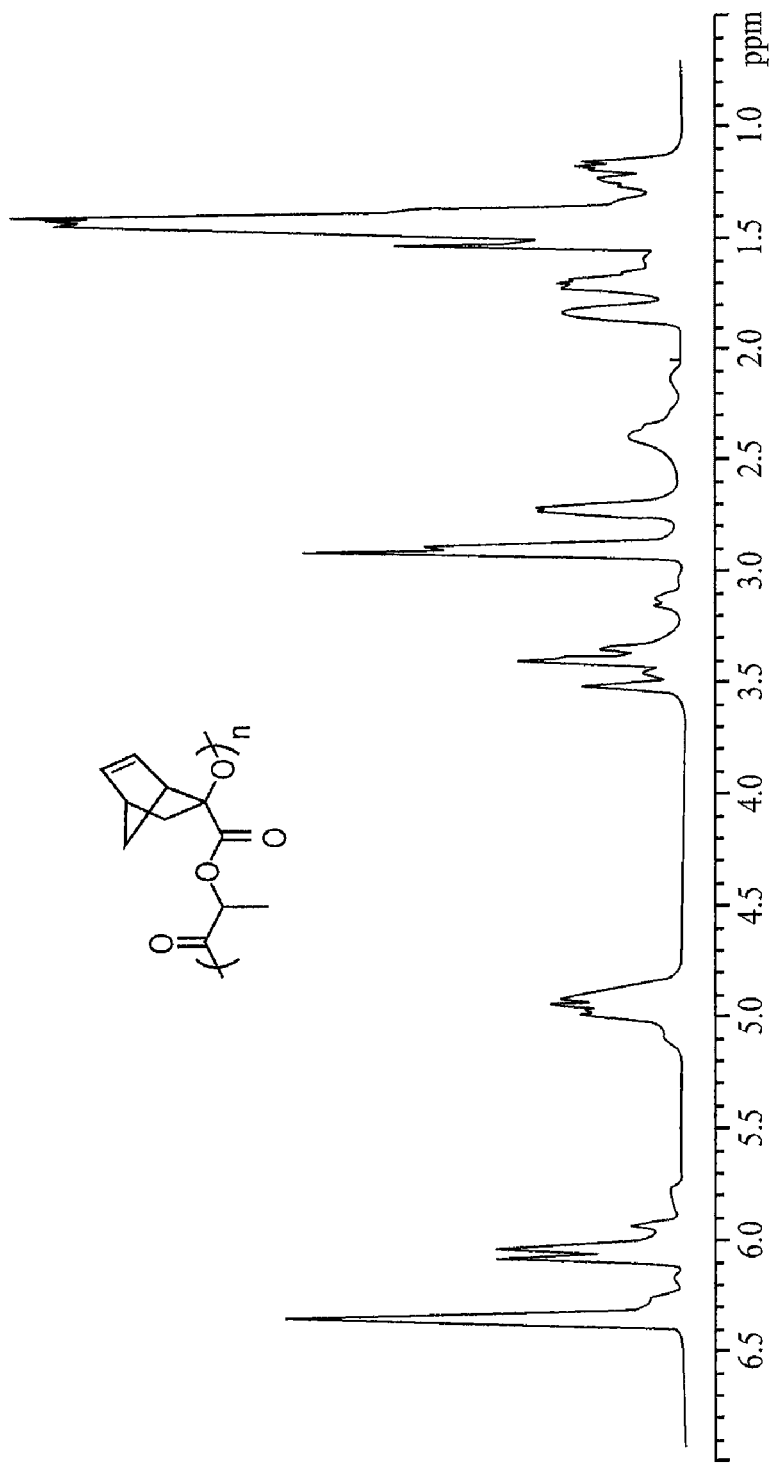
FIG. 5 is a NMR spectra graph of a lactide ring-opened homopolymer prepared from spiro[6-methyl-1,4-dioxane-2,5-dione-3,2'-bicyclo[2.2.1]hept[5]ene] (poly(oxy-1-oxoethylene-2-bicyclo[2.2.1]hept-5-ene)).

The reaction can be optimized when performed at −20° C. as opposed to ambient temperature, wherein 94% conversion was achieved after 24 hours with relative molecular mass M$_n$=12.2 kg mol$^{-1}$ and PDI=1.27. $^1$H NMR spectra data for the prepared homopolymer can be seen in FIG. 5. This phenomenon is consistent with the bulky nature of the norbornene side group limiting the exothermicity of the polymerization reaction.

In this process stage, molecular weights of the resultant polymer could be controlled by increasing amount of the norbornene spiro lactide monomer relative to the catalyst and initiator amounts. Using less relative amounts of the initiator and catalyst (spiro[6-methyl-1,4-dioxane-2,5-dione-3,2'-bicyclo[2.2.1]hept[5]ene] 0.20 g, 1,5,7-triazabicyclo[4.4.0]dec-5-ene (TBD) 0.22 mg, benzyl alcohol 0.33 μL and anhydrous CH$_2$Cl$_2$ 0.96 mL) could achieve as high as relative molecular mass M$_n$=33.6 kg mol$^{-1}$, PDI=1.63. The resulting homopolymer had a high molecular weight homopolymer (M$_n$ of 33.6 kg mol$^{-1}$ as compared to 12.2. kg mol$^{-1}$) and exhibited a glass transition temp (T$_g$) 113° C. as measure by DSC. The glass transition temperature associated with this polymer is significantly greater than known polylactide derivatives.

Because of the relatively higher Tg values compared to existing polylactides, this homopolymer can have applications in areas such as packaging materials, engineering plastics, materials for tissue engineering, and the like. Furthermore, this monomer can be used in copolymerizations with other cyclic esters such as lactide, glycolide, caprolactone, and the like, to prepare new materials with increased glass transition temperatures.

Norbornene Ring-Opened Homopolymer

Alternative to the lactide ring-opened homopolymer, spiro[6-methyl-1,4-dioxane-2,5-dione-3,2'-bicyclo[2.2.1]hept[5]ene] monomer derivative can be used to synthesize a norbornene ring-opened homopolymer (also shown in FIG. 2). Norbornene ring-opened homopolymers can be used to further synthesize other polymers.

Example 3

Preparation of Norbornene Ring-Opened Polymer

To prepare the norbornene-opened homopolymer (poly(8-methyl-6,9-dioxa-spiro[4.5]decane-7,10-dione-1,3-diylvinylene)), spiro[6-methyl-1,4-dioxane-2,5-dione-3,2'-bicyclo[2.2.1]hept[5]ene]monomer derivative can be subjected to ring-opening metathesis polymerization (ROMP). Using this approach, spiro[6-methyl-1,4-dioxane-2,5-dione-3,2'-bicyclo[2.2.1]hept[5]ene] monomer (0.20 g, 0.96 mmol) and 3$^{rd}$ generation Grubbs' catalyst (8.5 mg, 9.6 μmol) (prepared using a process similar to that described in Grubbs, *Angew. Chem., Int. Ed.* 41, p. 4035-37 (2002)) were added to a 20 mL vial. The vial was fitted with a septum and purged under nitrogen for a period of 10 minutes. Dichloromethane (4.8 mL) was then added via syringe through the septum to the vial under quick stirring. After 30 minutes, the reaction was then quenched by addition of excess (>20 equivalents) of ethyl vinyl ether. The polymer solution was precipitated from methanol to remove catalyst and ethyl vinyl ether. The formed solid polymer sample was vacuum dried overnight and analyzed using NMR, GPC and DSC.

The resultant norbornene ring-opened polymers having lactide ring side groups (poly(8-methyl-6,9-dioxa-spiro[4.5]decane-7,10-dione-1,3-diylvinylene)) had high molecular weights and narrow polydispersity indices. These homopolymers might be useful as engineering materials, for example, wherein grafted lactide rings could be used as crosslinkers to enhance polynorbornene's thermomechanical properties in conditions wherein crosslinking via double bonds would be either not viable or detrimental to material properties. The resulting norbornene-opened homopolymer (poly(8-methyl-6,9-dioxa-spiro[4.5]decane-7,10-dione-1,3-diylvinylene)) has the following structural formula:

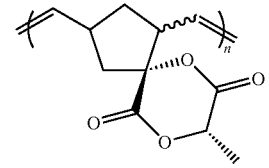

wherein n is an integer.

Figure 6:
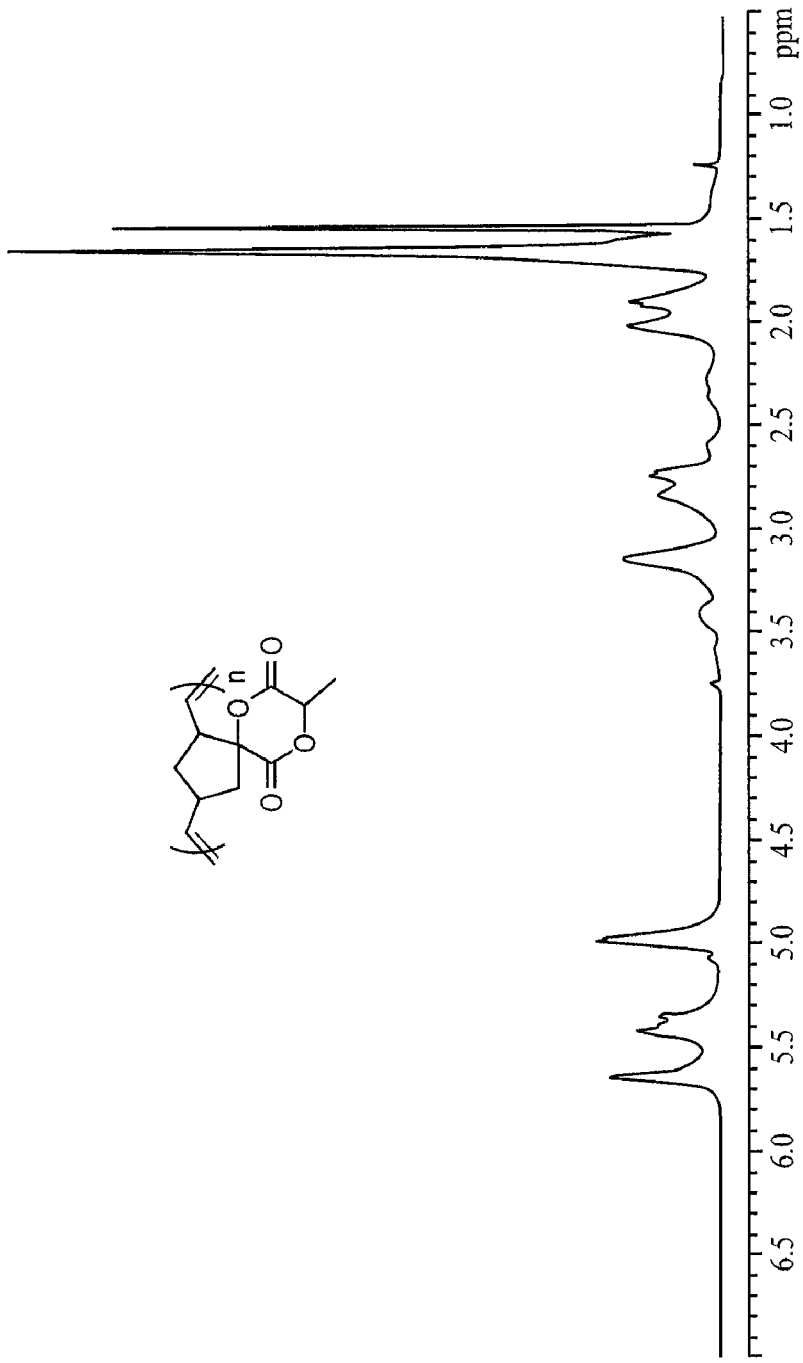
FIG. 6 is a NMR spectra graph of a norbornene ring-opened homopolymer prepared from spiro[6-methyl-1,4-dioxane-2,5-dione-3,2'-bicyclo[2.2.1]hept[5]ene] (poly(8-methyl-6,9-dioxa-spiro[4.5]decane-7,10-dione-1,3-diylvinylene)).

$^1$H NMR spectra data for the prepared homopolymer can be seen in FIG. 6.

It was further discovered that the molecular weight of poly(8-methyl-6,9-dioxa-spiro[4.5]decane-7,10-dione-1,3-diylvinylene) can be controlled by adjusting the ratio between the spiro[6-methyl-1,4-dioxane-2,5-dione-3,2'-bicyclo[2.2.1]hept[5]ene] monomer and the Grubbs' catalyst ([Ru]). Using polymerization conditions of 0.2 M of the monomer in CH$_2$Cl$_2$ for a reaction time of about 0.5-1 hour at ambient temperature and the reactions quenched with ethyl vinyl ether, ROMP prepares poly(8-methyl-6,9-dioxa-spiro[4.5]decane-7,10-dione-1,3-diylvinylene).

Performing the above process using varying ratios of monomer to catalyst, determining molecular weight and glass transition temperatures of the polymers, the data was set forth in the following table:

TABLE 1

Comparative Reaction Data using Varying Monomer to Catalyst Ratios

| Monomer (Formula (I)) to Grubbs' Catalyst [Ru] | M$_n$ (kg mol$^{-1}$) | M$_w$/M$_n$ | T$_g$ (° C.) |
|---|---|---|---|
| 50 | 14.0 | 1.04 | 168 |
| 100 | 27.2 | 1.09 | 191 |
| 200 | 48.5 | 1.10 | 191 |
| 300 | 62.8 | 1.16 | 191 |

TABLE 1-continued

Comparative Reaction Data using Varying Monomer to Catalyst Ratios

| Monomer (Formula (I)) to Grubbs' Catalyst [Ru] | $M_n$ (kg mol$^{-1}$) | $M_w/M_n$ | $T_g$ (° C.) |
|---|---|---|---|
| 500 | 91.6 | 1.12 | 189 |
| 1000 | 153.7 | 1.22 | 192 |

[Ru] = Grubbs' catalyst.

As can be seen from the data in Table 1, the greater the monomer/[Ru] value, the higher the molecular weight of the polymer and the higher the glass transition temperature. The resultant norbornene ring-opened polymer poly(8-methyl-6,9-dioxa-spiro[4.5]decane-7,10-dione-1,3-diylvinylene) exhibited a glass transition temperature ($T_g$) as high as 192° C. as measured using DSC. These homopolymers might be useful as engineering materials, for example, wherein grafted lactide rings could be used as crosslinkers to enhance polynorbornene's thermomechanical properties in conditions wherein crosslinking via double bonds would be either not viable or detrimental to material properties.

The bifunctional (dual) polymerization attributes associated with the monomer derivative of the invention can be utilized to further prepare various copolymers and composites. In one pathway, the norbornene ring can be opened and copolymerized with cyclooctadiene, and the resulting polymer with lactide ring side groups can in turn have the lactide rings opened to prepare additional composites.

Lactide-branched copolymers prepared from the monomer derivative of the invention can be synthesized by reacting the monomer with different alkenes. It may be possible to create copolymers using various cyclic olefins, e.g., cycloalkenes, aside from cyclooctadiene. In addition, varying lengths of backbone chain and structure can also be achieved by controlling the loading ratio of monomer to chain transfer agent, in addition to using different olefins.

Preparation of Lactide-Ring Functionalized polycyclooctadiene-co-polynorbornene copolymer poly(8-methyl-6,9-dioxa-spiro[4.5]decane-7,10-dione-1,3-diylvinylene)-co-poly(but-1-ene-1,4-diyl)

The spiro[6-methyl-1,4-dioxane-2,5-dione-3,2'-bicyclo[2.2.1]hept[5]ene] monomer derivative monomer of the invention can also be used to prepare copolymers poly(8-methyl-6,9-dioxa-spiro[4.5]decane-7,10-dione-1,3-diylvinylene)-co-poly(but-1-ene-1,4-diyl) having lactide ring side groups. This is illustrated as the first chemical reaction shown in FIG. 3 and can be performed using a modified ROMP procedure. The resulting polymer itself can further be used as a reactive polymer to synthesize other polymers such as shown as the second reaction in FIG. 3. Composite materials prepared using this and related polymers could be useful for the preparation of tough polylactide composites, high glass transition materials, or materials with improved water barrier properties.

Example 4

Figure 3:
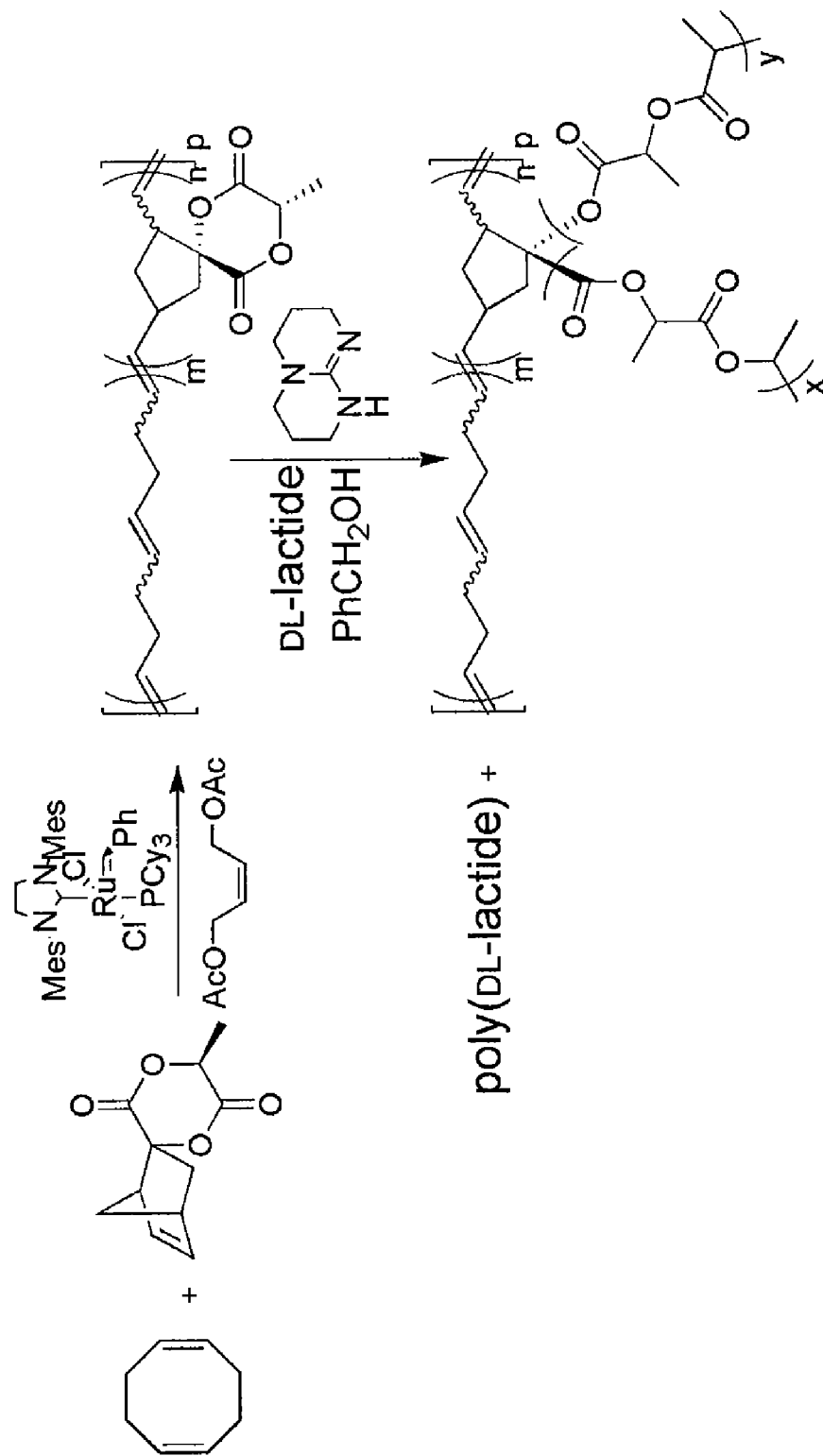
FIG. 3 is a multistep chemical reaction diagram showing 1) copolymerization of a cycloalkene with the spiro[6-methyl-1,4-dioxane-2,5-dione-3,2'-bicyclo[2.2.1]hept[5]ene] monomer derivative of the invention using a second generation Grubbs' catalyst with a chain transfer agent, and 2) reaction of the copolymer with DL-lactide to prepare a polylactide-based composite, according to one embodiment of the invention.

Preparation of Poly(8-methyl-6,9-dioxa-spiro[4.5]decane-7,10-dione-1,3-diylvinylene)-co-poly(but-1-ene-1,4-diyl) Copolymer Poly(8-methyl-6,9-dioxa-spiro[4.5]decane-7,10-dione-1,3-diylvinylene)-co-poly(but-1-ene-1,4-diyl) having lactide ring side groups can be prepared as illustrated in the first reaction shown in FIG. 3 using a second Generation Grubbs' catalyst in combination with a chain transfer agent. In the dry box, a catalyst/chain transfer agent solution was initially prepared by adding cis-2-butene-1,4-diol diacetate (301 µL, 1.91 mmol), second generation Grubbs' catalyst (32.4 mg, 38.2 µmol) and dichloromethane (40 mL) to a vial. Spiro[6-methyl-1,4-ioxane-2,5-dione-3,2'-bicyclo[2.2.1]hept[5]ene monomer was then added into a 150 mL pressure vessel (0.595 g, 2.86 mmol), along with 1,5-cyclooctadiene (10.0 g, 92.4 mmol), dichloromethane (30 mL) and a stir bar. The stock solution (10 mL) was added to the pressure vessel to initiate polymerization at room temperature. After a period of about 20 hours, the polymerization was quenched by addition of excess (>20 equivalents) of ethyl vinyl ether. A portion of the solution was then evacuated to dryness and analyzed by H NMR and GPC. The remainder of polymer solution was precipitated from methanol twice to remove catalyst and ethyl vinyl ether. The formed solid polymer was vacuum dried overnight and analyzed by NMR and GPC.

The resultant lactide ring functionalized copolymer had the following structural formula:

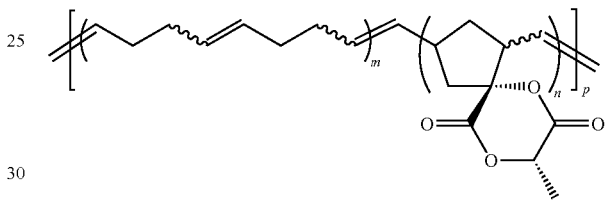

wherein m, n and p are each integers.

This copolymer is per se useful as reactive intermediate polymers for synthesis of other polymers wherein the lactide ring groups on the backbone can be used, e.g., cross-linking. This copolymer (SEC: PS stnd: $M_n$=46.6 kg mol$^{-1}$, $M_w/M_n$=1.69) exhibited a soft consistency. Composite materials prepared using this and related polymers could be useful for the preparation of tough polylactide composites, high glass transition materials, or materials with improved water barrier properties.

Composite: Open Lactide-Branched Polycyclooctadiene/Norbornene Polymer Units in Combination with D,L-lactide Poly(8-methyl-6,9-dioxa-spiro[4.5]decane-7,10-dione-1,3-diylvinylene)-co-poly(but-1-ene-1,4-diyl) of Example 4 can then itself be further used to prepare a composite material composed of poly-DL-lactide and polycyclooctadiene-co-polynorbornene-branch-polylactide (see FIG. 3).

Example 5

Preparation of Poly(8-methyl-6,9-dioxa-spiro[4.5]decane-7,10-dione-1,3-diylvinylene)-co-poly(but-1-ene-1,4-diyl)-branch-poly(DL-lactide)-blend-poly(DL-lactide)) Composite As depicted in the second reaction shown in FIG. 3, the poly(8-methyl-6,9-dioxa-spiro[4.5]decane-7,10-dione-1,3-diylvinylene)-co-poly(but-1-ene-1,4-diyl) of Example 4 (about 20 wt %) can be reacted with DL-lactide (about 80 wt %) via ROP using 1,5,7-triazabicyclo[4.4.0]dec-5-ene (TBD) as the catalyst and benzyl alcohol as the initiator.

The poly(8-methyl-6,9-dioxa-spiro[4.5]decane-7,10-dione-1,3-diylvinylene)-co-poly(but-1-ene-1,4-diyl) of Example 4 (1.0 g), DL-lactide (4.0 g, 27.8 mmol), benzyl alcohol (28.7 µL, 0.277 mmol), dichloromethane (40 mL) and a stir bar were added to a 150 mL vial. To the vial, a solution of 1,5,7-triazabicyclo[4.4.0]dec-5-ene (TBD) (3.9 mg, 28.0 µmol) in dichloromethane (1 mL) was added to initiate lactide ring-opening ROP polymerization. The polymerization reaction was conducted in an ice bath for a period of about 1 hour, followed by quenching with excess (>10 equivalents) benzoic acid. A portion of the solution was evacuated to dryness and analyzed using $^1$H NMR and GPC. The remaining polymer solution was vacuum dried overnight and analyzed by NMR, GPC and the tensile properties were tested.

In a separate experiment, a composite composed of poly (DL-lactide) in combination with poly(8-methyl-6,9-dioxaspiro[4.5]decane-7,10-dione-1,3-diylvinylene)-co-poly(but-1-ene-1,4-diyl)-branch-poly(DL-lactide) (SEC: $M_n$=48.7 kg mol$^{-1}$, $M_w/M_n$=2.89) was compression-molded at 120° C. into translucent films. Further, the product exhibited relatively enhanced toughness. As a cost-effective processing advantage, it may be possible that using only a relatively minor amount of the polymer portion of the composite need be present to significantly effect the resulting material properties.

Comparative Composite Data

A comparative binary blend composite was prepared containing the combination of polylactide with a polycyclooctadiene. The mechanical properties of the binary blend were then compared to a composite prepared according to the invention containing poly(8-methyl-6,9-dioxa-spiro[4.5]decane-7,10-dione-1,3-diylvinylene)-co-poly(but-1-ene-1,4-diyl)-branch-poly(DL-lactide)-blend-poly(DL-lactide) as shown in FIG. 3.

Example 6

Preparation of Binary Blend Composite Having Polycyclooctadiene and PLA

In a separate reaction and process similar to that described above in Example 5, poly(1,5-cyclooctadiene) homopolymer (($M_n$=44.9 kg mol$^{-1}$, $M_w/M_n$=1.70, 1.0 g) was reacted with DL-lactide (4.0 g) using ROP, TBD catalyst (3.9 mg) and benzyl alcohol initiator (28.7 µL), to prepare another composite, polycyclooctadiene and PLA ($M_n$=34.5 kg mol$^{-1}$, $M_w/M_n$=1.88). This binary blend composite can be compression-molded at 120° C. into opaque films.

Comparison Between Composite Material of Example 5 and Composite Material of Example 6

Films prepared from the composite of Example 5 by compression-molding at 120° C. were compared to films prepared under the same process conditions from the comparative Example 6 (polycyclooctadiene/PLA) composite and evaluated. SEM data revealed significant differences in morphology.

Figure 7A:
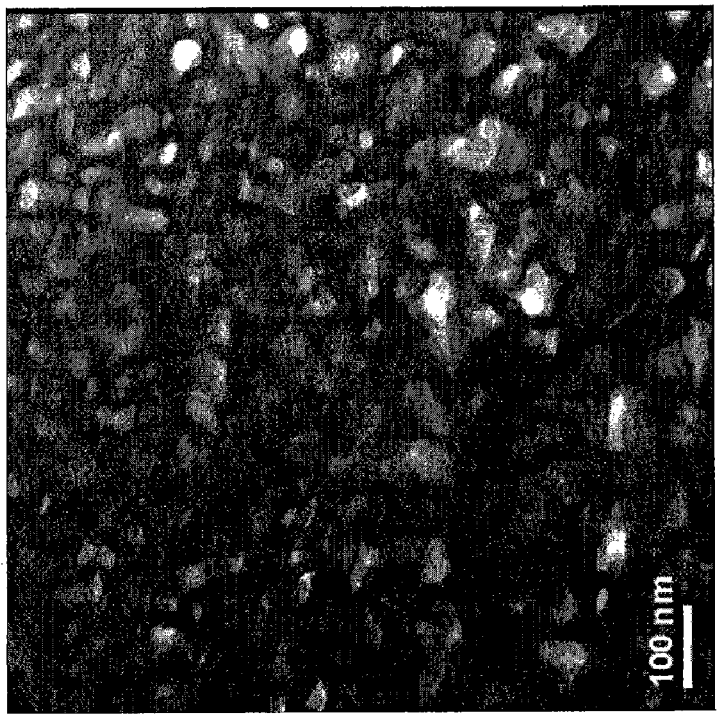
FIG. 7 is a pair of SEM images (A being secondary electron image and B being backscattered electron image) of the composite material poly(8-methyl-6,9-dioxa-spiro[4.5]decane-7,10-dione-1,3-diylvinylene)-co-poly(but-1-ene-1,4-diyl)-branch-poly(DL-lactide)-blend-poly(DL-lactide) according to one embodiment of the invention.
Figure 7B:
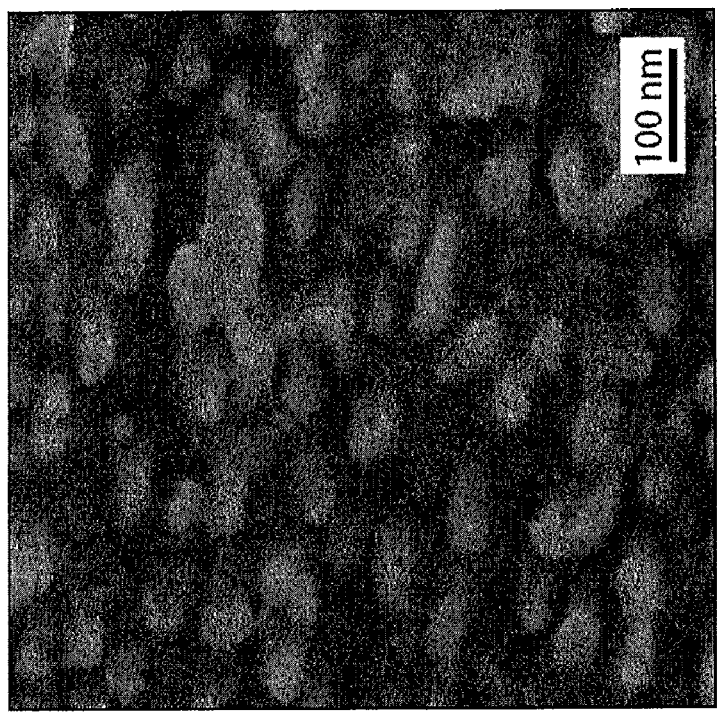
Figure 8B:
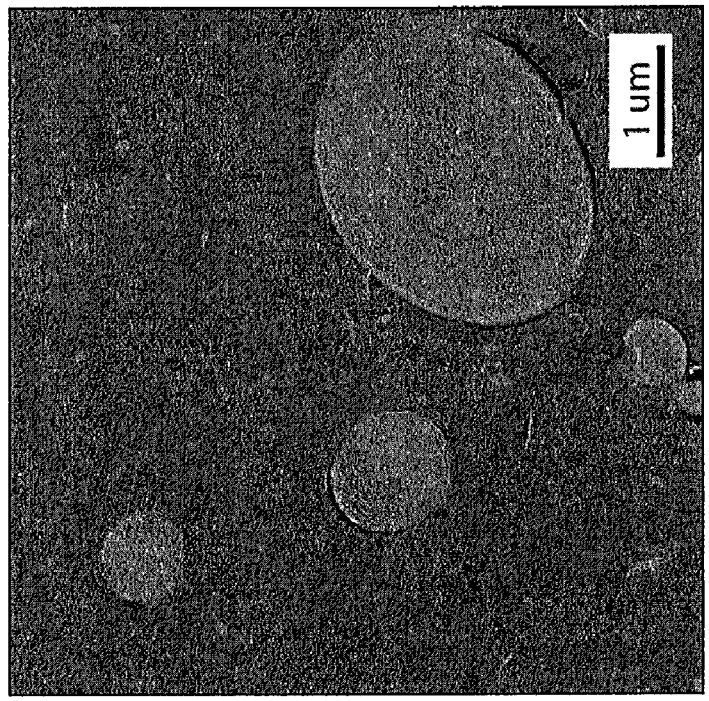
FIG. 8 is a pair of SEM images (A being secondary electron image and B being backscattered electron image) of the binary blends of polycyclooctadiene and poly(DL-lactide) according to one embodiment of the invention.
Figure 8A:
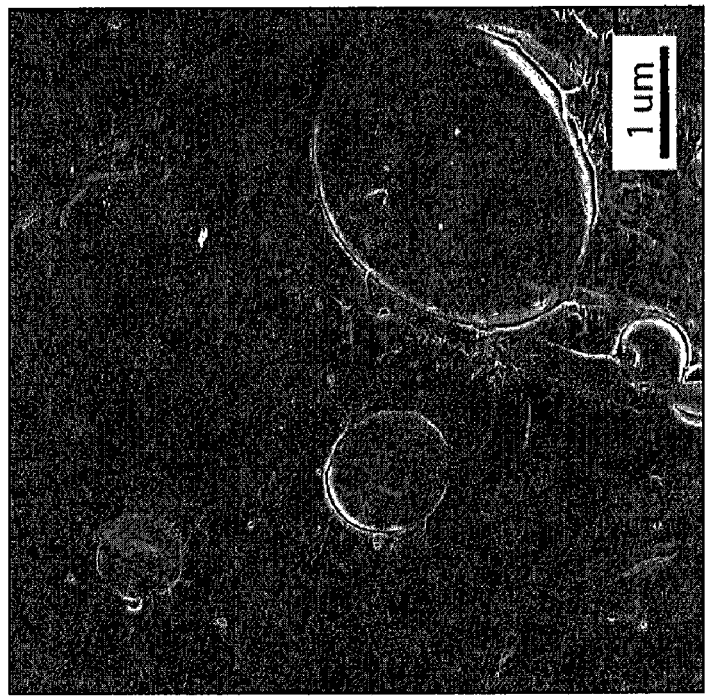
Figure 9:
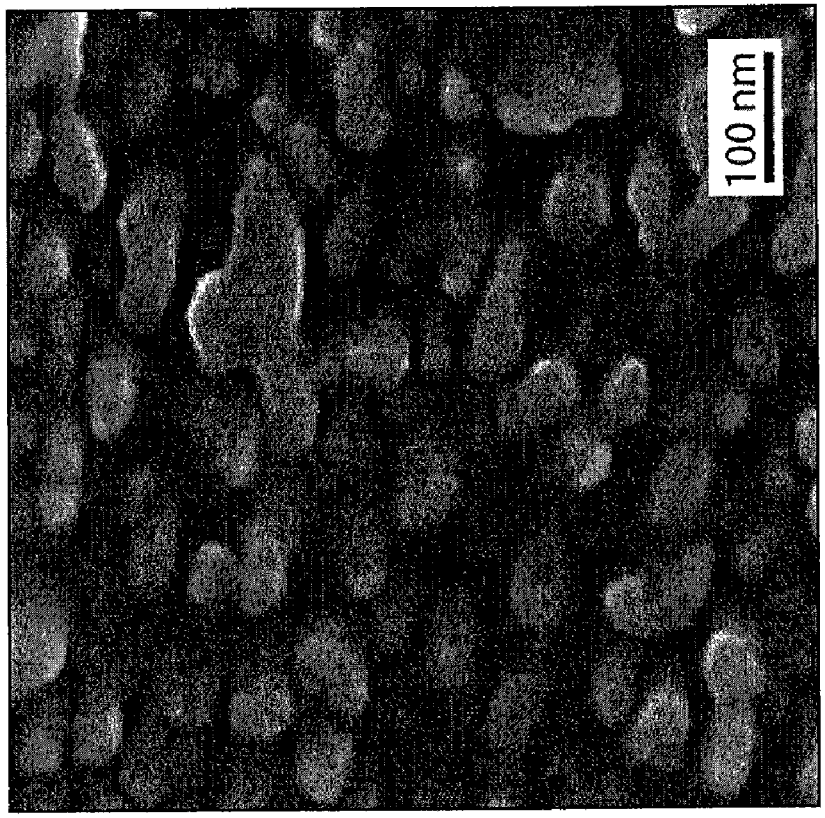
FIG. 9 is a TEM image of a thin section of composite material poly(8-methyl-6,9-dioxa-spiro[4.5]decane-7,10-dione-1,3-diylvinylene)-co-poly(but-1-ene-1,4-diyl)-branch-poly(DL-lactide)-blend-poly(DL-lactide) according to one embodiment of the invention.

Referring now to the SEM images shown in FIG. 8, the Example 6 composite exhibited macrophase separated domains of PLA and polycyclootadiene, whereas the composite of Example 5 (see images A and B in FIG. 7) exhibited nanoscale domains of polycyclooctadiene domains. Nanophase separation was confirmed using TEM and as shown in FIG. 9. Small-angle x-ray analysis of the Example 5 composite showed principal reflection with a domain spacing of about 45 nm, which was consistent with polycyclooctadiene/PLA chains intimately mingled with PLA homopolymer.

Figure 10:
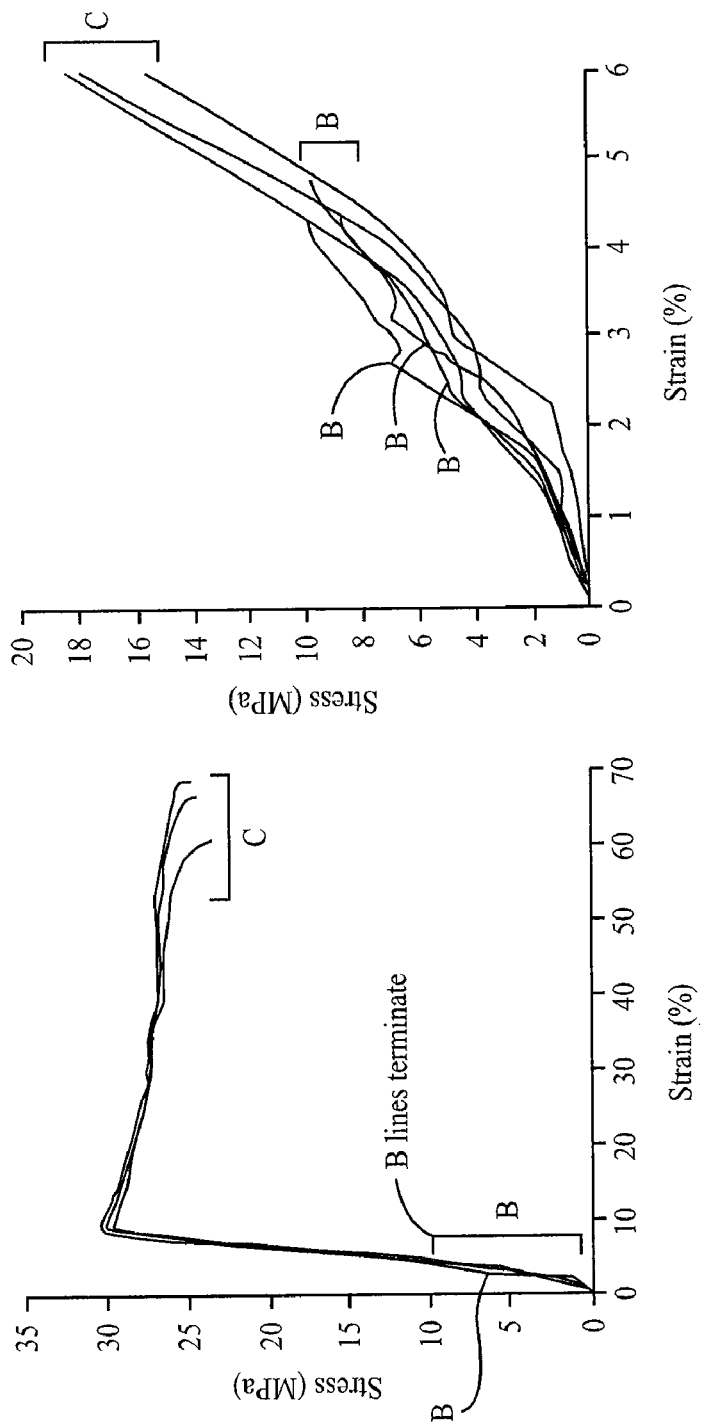
FIG. 10 is the comparative tensile strength data for the composite material poly(8-methyl-6,9-dioxa-spiro[4.5]decane-7,10-dione-1,3-diylvinylene)-co-poly(but-1-ene-1,4-diyl)-branch-poly(DL-lactide)-blend-poly(DL-lactide) ("C") and binary blends of polycyclooctadiene and poly(DL-lactide) ("B").

Tensile deformation experiments were carried out at room temperature using a MINIMAT™ instrument (available from Rheometrics Scientific, Inc., Piscataway, N.J.) operated at a cross-head speed of 5 mm/min. The sample gauge length was 5 mm, the gauge width was 3 mm, and the gauge thickness was around 0.4 mm. Elongation at break was measured at 65% for the Example 5 composite, with a tensile strength of 24 MPa and tensile toughness of 16 MJ m$^{-3}$. It is believed that the presence of the Example 5 copolymer between the PLA homopolymer in the composite and the rubber phase reduced interfacial tension and thus increased interfacial adhesion thereby improving mechanical properties of the material. Comparative composite data was based on the measured mechanical properties as set forth in FIG. 10 and the following table:

TABLE 2

Comparative Mechanical Strength Data of Example 5 Composite and Example 6 Composite

| Property | Composite Example 5 | Composite Example 6 |
|---|---|---|
| Elongation at break (%) | 65 | 4 |
| Tensile strength at break (MPa) | 24 | 9 |
| Young's Modulus (MPa) | 528 | 418 |
| Tensile toughness (MJ m$^{-3}$) | 16 | 0.2 |

The thermoformable, partially biodegradable polylactide-based composite material prepared according to the invention can have a wide variety of applications. Products and packaging that the invention can be used with include those which are both unlikely and likely to experience elevated temperature conditions—either environmentally or content-wise. The invention is particularly useful for use in products and packaging wherein the chemical and physical attributes associated with polylactides are desired, such as renewability, biocompatibility, biodegradability, and thermoformability, and wherein the product or packaging would likely experience high temperature conditions or contents without significant adverse effects to the structural integrity of the product or package. In addition to these attributes, the invention can be used to prepare such polylactide-containing or polylactide-derived materials which also exhibit enhanced durability and toughness, e.g., resistance to cracking, as well as controlling liquid barrier (e.g., water transport) properties. All of these characteristics are significant in consumer product and packaging applications.

Product and packaging products can be prepared using a wide variety of conventional thermoforming techniques and equipment readily available to those skilled in the plastics manufacturing field. For example, injection molding and blow molding techniques can be used, as well as thermoforming processes and equipment to prepare laminated and monolayer films.

INDUSTRIAL APPLICABILITY

The invention can be used in a variety of ways within polymer synthesis processes and as part of the preparation of thermoformable polymers which in turn can be used in a wide variety of industrial applications. For instance, the polymers prepared according to the invention can be used in medical products and packaging. The invention can be used to produce a wide variety of thermoformable products and packaging wherein durability and toughness are also desired.

The invention herein above has been described with reference to various and specific embodiments and techniques. The full text of any patents, patent applications and literature cited herein above are incorporated by reference in their entirety. It will be understood by one of ordinary skill in the art, however, that reasonable variations and modifications may be made with respect to such embodiments and techniques without substantial departure from either the spirit or scope of the invention defined by the following claims.

What is claimed is:

1. A lactide monomer derivative, spiro[6-methyl-1,4-dioxane-2,5-dione-3,2'-bicyclo[2.2.1]hept[5]ene], having the following structural formula:

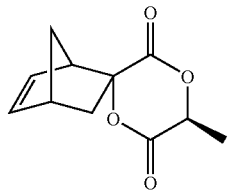

and stereoisomers thereof.

2. A process for preparing spiro[6-methyl-1,4-dioxane-2,5-dione-3,2'-bicyclo[2.2.1]hept[5]ene] comprising:
   a) reacting L-lactide with N-bromosuccimide to prepare a brominated intermediate compound 3-bromo-3,6-1,4-dioxane-2,5-dione;
   b) reacting 3-bromo-3,6-1,4-dioxane-2,5-dione with a tertiary amine to prepare 3-methyl-6-methylene-1,4-dioxane-2,5-dione; and
   c) reacting 3-methyl-6-methylene-1,4-dioxane-2,5-dione with a cyclopentadiene to prepare spiro[6-methyl-1,4-dioxane-2,5-dione-3,2'-bicyclo[2.2.1]hept[5]ene].

3. The process according to claim 2, wherein said tertiary amine is triethylamine.

* * * * *